United States Patent

Wiesent et al.

[11] Patent Number: 5,706,324
[45] Date of Patent: Jan. 6, 1998

[54] X-RAY COMPUTED TOMOGRAPHY APPARATUS HAVING MARKS FOR GEOMETRICAL IMAGE CORRELATION

[75] Inventors: Karl Wiesent, Erlangen; Guenter Schwierz, Neunkirchen, both of Germany

[73] Assignee: Siemens Aktiengesellschaft, Munich, Germany

[21] Appl. No.: 626,568

[22] Filed: Apr. 2, 1996

[30] Foreign Application Priority Data

Apr. 5, 1995 [DE] Germany ............ 195 12 819.2

[51] Int. Cl.⁶ ............................................. A61B 6/03
[52] U.S. Cl. .................................. 378/4; 378/163
[58] Field of Search ................................ 378/4, 18, 205, 378/162, 163, 164

[56] References Cited

U.S. PATENT DOCUMENTS

| | | | |
|---|---|---|---|
| 3,952,194 | 4/1976 | Bayonnet | 378/61 |
| 4,319,136 | 3/1982 | Jinkins | 378/4 |
| 4,341,220 | 7/1982 | Perry | 128/630 |
| 4,608,977 | 9/1986 | Brown | 128/303 B |
| 4,618,978 | 10/1986 | Cosman | 378/164 |
| 4,782,502 | 11/1988 | Schulz | 378/18 |
| 4,838,265 | 6/1989 | Cosman et al. | 128/303 B |
| 5,377,250 | 12/1994 | Hu | 378/15 |
| 5,436,950 | 7/1995 | Pauli et al. | 378/4 |
| 5,442,674 | 8/1995 | Picard et al. | 378/20 |

Primary Examiner—David P. Porta
Assistant Examiner—David Vernon Bruce
Attorney, Agent, or Firm—Hill, Steadman & Simpson

[57] ABSTRACT

In an x-ray computed tomography apparatus with low radiation exposure to the patient, marks are additionally imaged during scanning of the patient, by which the geometry of the image can be determined. The marks are arranged above and/or below a region of interest in the measurement field on rings and are imaged by the x-ray beam.

15 Claims, 3 Drawing Sheets

X-RAY COMPUTED TOMOGRAPHY APPARATUS HAVING MARKS FOR GEOMETRICAL IMAGE CORRELATION

BACKGROUND OF THE INVENTION

1. Field of the Invention

The present invention is directed to an x-ray computed tomography apparatus of the type having a C-arm carrying an x-ray source and a radiation detector, which rotates around an examination subject for producing an image.

2. Description of the Prior Art

For the production of computed tomographic exposures, e.g. for the three-dimensional image reconstruction of an object under examination, a C-arm apparatus can be used, in which the x-ray source is located at one end and the radiation detector is located at the other end of a C-arm, whereby the x-ray source and the radiation detector are rotated around a measurement field in which the object under examination is located. Due to unavoidable mechanical instabilities, the coordinates of the source and the radiation detector are not known precisely, and typically will change during the course of the investigation. An x-ray image intensifier can be provided as the radiation detector.

SUMMARY OF THE INVENTION

It is an object of the present invention to provide an x-ray computed tomography apparatus wherein disturbances of the geometric coordination of the source and the radiation detector can be eliminated.

In the x-ray computed tomography apparatus according to the invention, during the exposure of the object under examination marks are also imaged which serve as orientation marks for detecting unstable coordinates. The marks are arranged so that the skin dose is reduced to a minimum. The marks can be imaged in the central part of the detector, so that if an x-ray image intensifier is used, the geometric distortion of the x-ray image amplifier image is uncritical.

DESCRIPTION OF THE DRAWINGS

FIG. I is a schematic illustration of a marking arrangement employed in the inventive apparatus for the explanation of the inventive concept.

DESCRIPTION OF THE PREFERRED EMBODIMENTS

Figure 1:
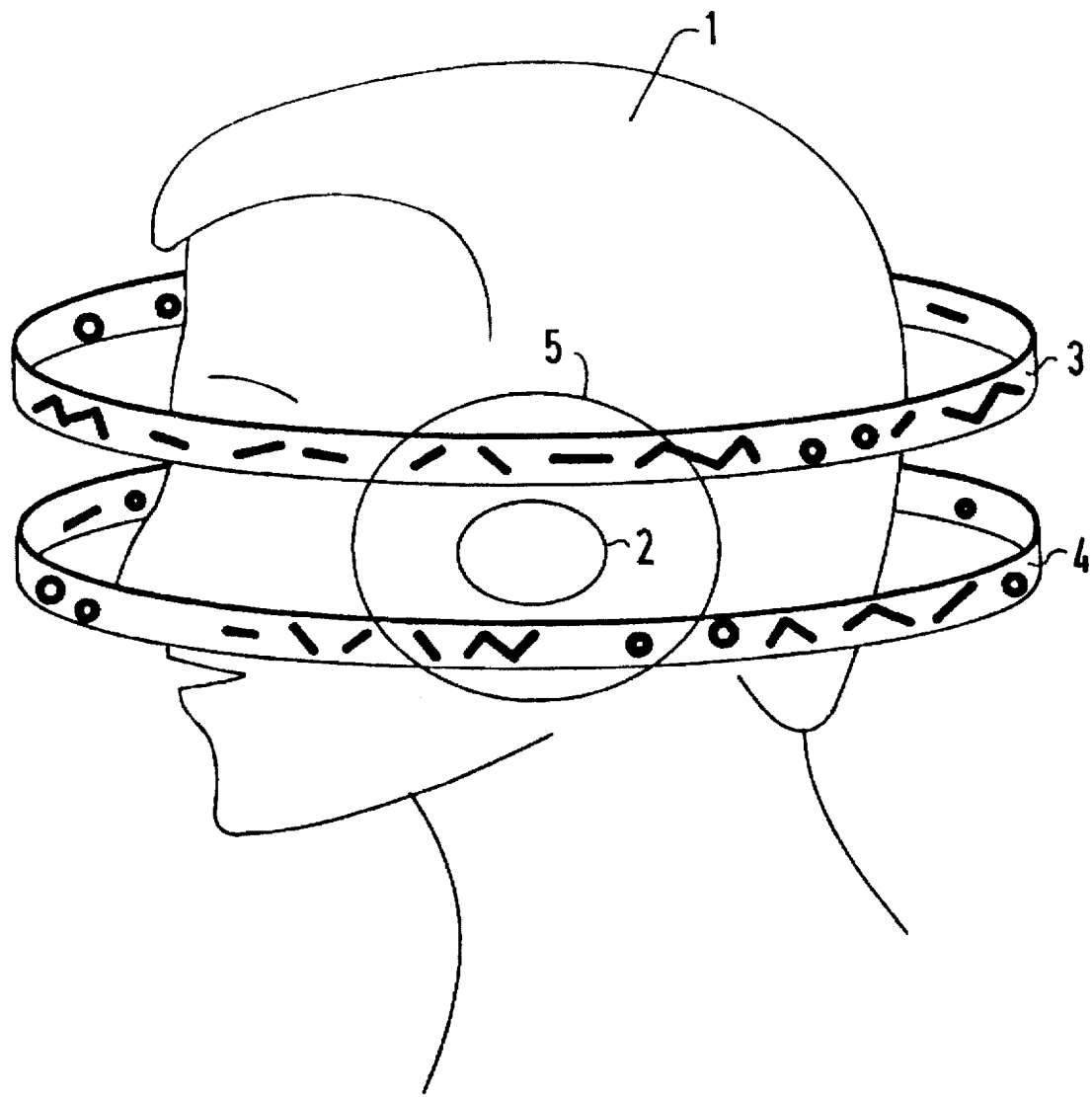

In FIG. 1 an object 1 under examination (the head of a patient)is represented; an image of a region of interest 2 thereof is to be produced by means of computed tomography. For enabling corrective measures to be undertaken regarding coordinate changes which may occur during image production, two rings 3 and 4 are arranged above and below the region of interest 2 in the measurement field 5, which carry marks which are also present (visible) in the image.

Figure 2:
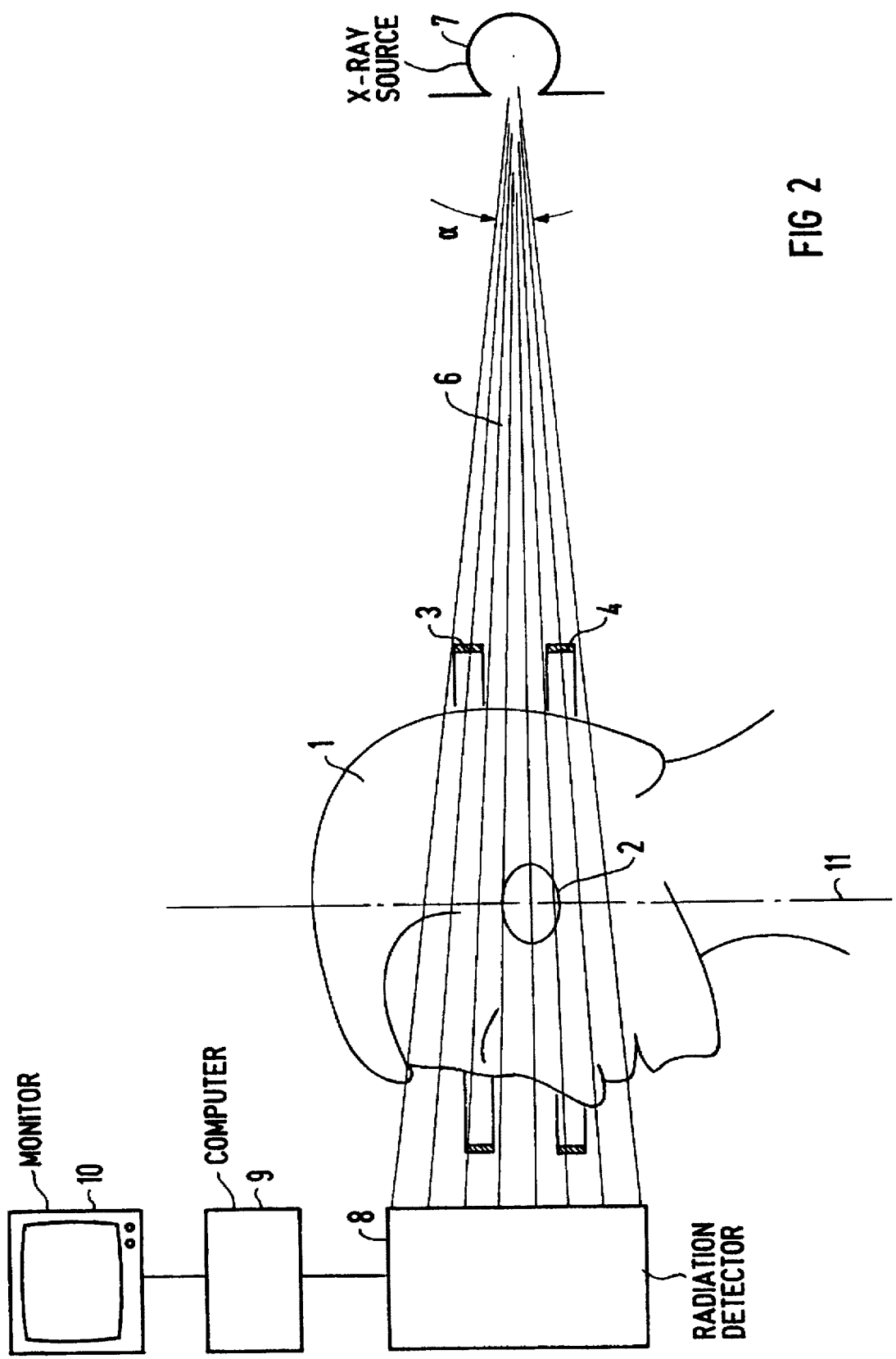
FIG. 2 shows the basic components of a computed tomography apparatus for generating an image using the inventive concept explained in FIG. 1.

FIG. 2 shows that the object 1 under examination is transirradiated by a cone-shaped beam of x-rays 6, proceeding from the focus of a source 7 of x-ray radiation. After it has penetrated the measurement field 5, it is incident on a planar, high-resolution detector 8, e.g. an x-ray image intensifier, whose output signals are supplied to a computer 9, which computes a three-dimensional image of the measurement field 5, in particular the region 2. The visual display on a monitor 10 ensues by means of suitable display programs known in the art. The measurement unit, formed by the x-ray source 7 and the detector 8, is rotated around the object 1 under examination and thus around the measurement field 5, this rotation taking place about an axis 11, so that the measurement field 5 is transirradiated in various directions.

FIGS. 1 and 2 show that the rings 3 and 4, having marks (not illustrated in FIG. 2), lie outside the region 2, but are still directly penetrated by the x-ray beam 6, so that the marks are imaged on the detector 8. The marks permit a precise determination of the photographic geometry, and the radiation dose is thereby low outside of the region of interest 2, since the beam spread angle a of the x-ray beam 6 can be kept small.

The marks can be attached to two bands parallel to the plane of the focus path above and below the region 2. They can in this case be made of a high-contrast material, e.g., lead, since they are not imaged in the relevant (diagnostic) image area. The beam spread angle a must be only somewhat larger than is required for imaging the region 2, but it is significantly smaller than would be required for a complete transirradiation of the object 1 under examination. The rings 3 and 4 may be annular, such as circular, but may alternatively be formed as polygons. They must be arranged rigidly to one another, which can be achieved by means of connection with a few rigid, radiolucent cross-braces made, e.g., of titanium.

Figure 3:
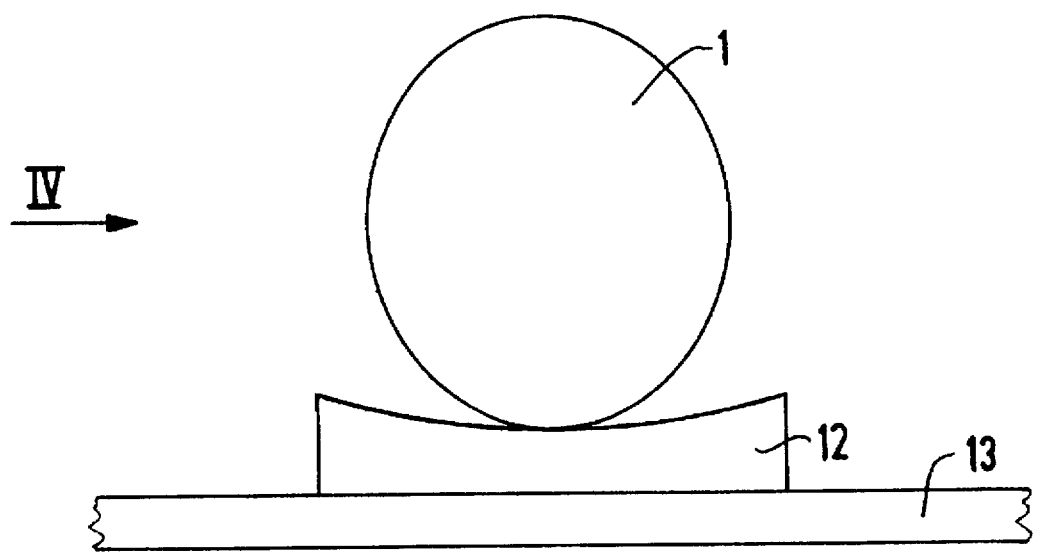
FIGS. 3 and 4 respectively illustrate details of the computed tomography apparatus of FIG. 2.
Figure 4:
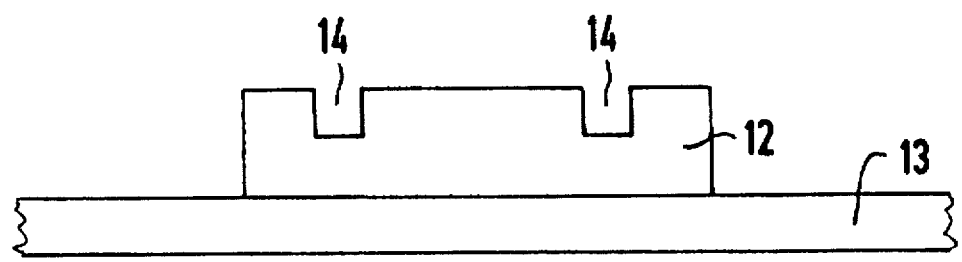

FIG. 3 shows that the object 1 under examination is positioned on a cushion 12 that lies on a bed 13. The bed 13 is shown in FIG. 3 from the front and in FIG. 4 from the side. It can be seen in FIG. 4 that the cushion 12 has grooves 14 into which the rings 3 and 4 fit. The rings 3 and 4 are not shown in FIG. 3. The object 1 under examination is not shown in FIG. 4. The grooves 14 avoid rings 3 and 4 and having to be conducted around the bed 13. Instead, the rings 3 and 4 are placed over the object 1 under examination and then, when the object under examination 1 is lying on the cushion 12, are held in place by this object.

Although modifications and changes may be suggested by those skilled in the art, it is the intention of the inventors to embody within the patent warranted hereon all changes and modifications as reasonably and properly come within the scope of their contribution to the art.

We claim as our invention:

1. In an x-ray computed tomography apparatus having an x-ray source which emits an x-ray beam that penetrates an examination subject in a measurement field and which produces an x-ray image on a radiation detector while the x-ray source and the radiation detector are rotated around said examination subject, said measurement field including a region of interest, the x-ray detector converting the x-ray image into electrical signals, and means for generating an image of said examination subject from said electrical signals, the improvement comprising:
    a plurality of marks, separate from said examination subject, respectively producing mark images which are present in said x-ray image; and
    means for annularly arranging said marks relative to said examination subject above said region of interest in said measurement field.

2. The improvement of claim 1 wherein said means for annularly arranging said marks comprises a carrier on which said marks are disposed adapted to be worn by said examination subject.

3. The improvement of claim 1 wherein said means for arranging said marks comprise a circular ring on which said marks are disposed.

4. The improvement of claim 1 wherein said means for arranging said marks comprise a polygon on which said marks are disposed.

5. The improvement of claim 1 wherein said means for arranging said marks comprise, an annular carrier on which said marks are disposed and adapted to be worn by said examination subject, and said improvement further comprising a cushion for said examination subject having a groove therein for accepting said carrier.

6. In an x-ray computed tomography apparatus having an x-ray source which emits an x-ray beam that penetrates an examination subject in a measurement field and which produces an x-ray image on a radiation detector while the x-ray source and the radiation detector are rotated around said examination subject, said measurement field including a region of interest, the x-ray detector converting the x-ray image into electrical signals, and means for generating an image of said examination subject from said electrical signals, the improvement comprising:

a plurality of marks, separate from said examination subject, respectively producing mark images which are present in said x-ray image; and means for annularly arranging said marks relative to said examination subject below said region of interest in said measurement field.

7. The improvement of claim 6 wherein said means for annularly arranging said marks comprises a carrier on which said marks are disposed adapted to be worn by said examination subject.

8. The improvement of claim 6 wherein said means for arranging said marks comprise a circular ring on which said marks are disposed.

9. The improvement of claim 6 wherein said means for arranging said marks comprise a polygon on which said marks are disposed.

10. The improvement of claim 6 wherein said means for arranging said marks comprise an annular carrier on which said marks are disposed and adapted to be worn by said examination subject, and said improvement further comprising a cushion for said examination subject having a groove therein for accepting said carrier.

11. In an x-ray computed tomography apparatus having an x-ray source which emits an x-ray beam that penetrates an examination subject in a measurement field and which produces an x-ray image on a radiation detector while the x-ray source and the radiation detector are rotated around said examination subject, said measurement field including a region of interest, the x-ray detector converting the x-ray image into electrical signals and means for generating an image of said examination subject from said electrical signals, the improvement comprising:

a plurality of marks, separate from said examination subject, respectively producing mark images which are present in said x-ray image; and means for annularly arranging said marks related to said examination subject above and below said region of interest in said measurement field.

12. The improvement of claim 11 wherein said means for annularly arranging said marks comprises a carrier on which said marks are disposed adapted to be worn by said examination subject.

13. The improvement of claim 11 wherein said means for arranging said marks comprise a circular ring on which said marks are disposed.

14. The improvement of claim 11 wherein said means for arranging said marks comprise a polygon on which said marks are disposed.

15. The improvement of claim 11 wherein said means for arranging said marks comprise an annular carrier on which said marks are disposed and adapted to be worn by said examination subject, and said improvement further comprising a cushion for said examination subject having a groove therein for accepting said carrier.

* * * * *